United States Patent [19]

Stern et al.

[11] 4,058,598

[45] Nov. 15, 1977

[54] CYTOMEGALOVIRUS ATTENUATION METHOD AND VACCINE

[76] Inventors: Harold Stern, St. Georges Hospital, University of London, London, S.W.1, England; Stephen Dyonis Elek, Av. de Cour 155, Lausanne, Switzerland, 1007

[21] Appl. No.: 533,502

[22] Filed: Dec. 17, 1974

[30] Foreign Application Priority Data

Oct. 18, 1974 United Kingdom ............... 45203/74

[51] Int. Cl.² ........................ A61K 39/12; C12K 7/00
[52] U.S. Cl. ........................................ 424/89; 195/1.3
[58] Field of Search ............................ 424/89; 195/1.3

[56] References Cited

U.S. PATENT DOCUMENTS 3,959,466  5/1976  Plotkin .................................. 195/1.3

OTHER PUBLICATIONS

Probstmeyer et al., Chem. Abst., vol. 66 (1967) p. 92561x.
McAllister et al., Chem. Abst., vol. 66 (1967) p. 113,099v.
Elek et al., Lancet, Jan. 5, 1974, pp. 1-5.

*Primary Examiner*—Sam Rosen
*Attorney, Agent, or Firm*—Donald Brown

[57] ABSTRACT

An attenuated strain of cytomegalovirus is prepared by serial passage in human tissue culture cells. The stain of virus so attenuated is incorporated into vaccines and used for developing immunity in humans against infections with cytomegalovirus.

16 Claims, No Drawings

CYTOMEGALOVIRUS ATTENUATION METHOD AND VACCINE

This invention relates to attenuated strains of the cytomegalovirus (C.M.V.) and to vaccines for developing immunity in humans against infections with C.M.V. In a further aspect the invention relates to a method of immunising humans by the use of such vaccines.

Cytomegalovirus is the most common known infections cause of mental retardation in infancy. Infection by C.M.V. is particularly frequent during pregnancy, since about 40% of women, at least in England and Wales, enter this state without antibodies, and are thus susceptible to infection. Infected women may excrete virus in the urine, on the cervix and in the milk.

Most of these congenital infections are asymptomatic or cause only minor illnesses, and yet a substantial proportion of the infected infants suffer irreversible brain damage, which could range from some degree of sensorineural deafness to subnormal intelligence. No chemotherapeutic treatment or vaccination against the infection has hitherto been recommended or successfully established experimentally, and the high incidence of the disease and the risk of its effects has remained a considerable hazard to the population.

It has been found that a live attenuated C.M.V. vaccine can be prepared which stimulates the production of complement-fixing (C.F.) and neutralising antibodies in susceptible individuals with very slight side-effects. The attenuation of the C.M.V. strain involves a considerable number of passages in tissue cultures particularly in human fibroblast cells to substantially reduce its pathogenicity but without loss of sufficient immunogenicity and infectivity. The attenuated strain prepared in this manner can be incorporated in injectable carriers to provide vaccines suitable for parenteral administration, for instance by the intradermal and subcutaneous route.

In one aspect therefore the present invention provides an attenuated strain of the cytomegalovirus which stimulates production of C.F. and neutralising antibodies in susceptible humans, when tested about 10 weeks after the subcutaneous administration of $10^4$ T.C.D.$_{50}$ units of the strain, without any significant side effects lasting longer than 1 to 2 weeks or detectable excretions of the virus from the test subjects. In a particular aspect such a strain is provided by serially passaging a cytomegalovirus isolate in susceptible cell cultures, in particular human fibroblast cell cultures, to yield a strain, the pathogenicity of which is of an acceptable level, but infectivity and immunogenicity are retained.

Any wild strain isolated from patients, or subclinical carriers, may be suitable for the attenuation procedure. It is convenient to start with C.M.V. strain Ad 169, also known as strain N.I.H. 76559, isolated from a subclinical carrier, namely by taking some adenoid tissue, in which the virus remains latent, and making tissue culture from this. In a short time the virus manifests itself in the cultures. Alternatively it can be isolated from the urine or by taking throat swabs and culturing from these.

The susceptible cell cultures suitable for serial passages according to the present invention include human cell cultures preferably without contaminating viruses or other microorganisms, such as mycoplasma, which show no oncological properties under the usual standard test conditions, e.g. the hamster pouch test. Primary and secondary human fibroblast cells are especially suitable for the purpose, such as the known embryonic fibroblasts (M.A.F.), foreskin fibroblasts and diploid embryonic lung fibroblast cells (H.E.L. or M.R.C.-5 Jacobs, J. P. et al. Nature 1970 227 168). These cultures are usually not capable of unlimited propagation and have virtually normal chromosome characteristics.

Human cells have been found to be necessary for C.M.V. since the virus is highly species specific and grows well only in human cells. Fibroblast cells are preferred for the purpose. With increasing number of passages it was found that the virus multiplies more quickly and becomes more adapted to tissue culture. Although a relatively low number of passages may be sufficient to reduce pathogenicity, normally at least 40 passages are carried out to provide an attenuated strain which is considered to be acceptable and safe for use.

It is advantageous to propagate the virus in more than one of these fibroblast cells. A passage history involving at least 8 passages in each of the above-mentioned types of cultures, i.e. M.A.F., human foreskin fibroblasts, H.E.L. and M.R.C.-5 cells, has been preferred. The resulting attenuated strain may be checked for freedom from extraneous organisms by culturing tests in various media favouring the growth of such microorganisms.

The infectivity and thus the active amount of viable viruses in the culture is tested by observing the cytopathic effect over a period, for instance in H.E.L. cells. Usually 2 to 10 fold serial dilutions are used and the effect calculated by the Reed-Muench (Reed, L. V. & Muench, H. (1938) Amer. J. Hyg. 27 493) formula. The values are expressed as T.C.D.$_{50}$ (tissue culture infective dose, which provides a cytopathic effect in 50% of the test number of cells).

Whilst the virus strain retains its ability to infect cells, its overall pathogenicity to the human host is reduced to an acceptable level. No detectable amounts of the virus must appear in throat washings or urine samples when tested on cell cultures within 4 weeks after the intradermal inoculation of $3 \times 10^5$ T.C.D.$_{50}$ units of the attenuated strain or after $10^4$ T.C.D.$_{50}$ units have been given subcutaneously. Some local lesions may appear at the site of inoculation, which usually reach their maximum 10 days after intradermal inoculation. However, it is more important that with $10^4$ T.C.D.$_{50}$ dosage given subcutaneously, only slight tenderness and aching may result in some patients around the 13th day, but such minimal side-effects would normally disappear within a week.

It is also relevant that no disturbance of the liver-function test was observed with $10^5$ T.C.D.$_{50}$ units (subc.) or $10^5$ T.C.D.$_{50}$ (intrader.), and only a minority of vaccinated individuals developed a temporary enlargement of the lymph glands in the neck, but no other effects or permanent damage can be observed with a strain attenuated according to the present invention.

The immunogenicity of the strain so prepared can be tested by determining complement-fixing antibodies by the standard microtitre technique. Neutralising antibodies can be assayed by the plaque reduction method. For instance, the majority of test patients developed C.F. antibody titres of at least 32, frequently around 64 or more, 4 to 8 weeks after subcutaneous inoculation with $10^4$ T.C.D.$_{50}$ units of the C.M.V. attenuated strain.

The reaction of the test subjects, who developed sufficient seropositivity after inoculation, to challenge tests with high dosages of the attenuated viruses has indicated that the immunogenicity conferred to the patients is similar in kind and degree to natural immunological protection, and would effectively prevent the re-occurrence of the disease. There is a sufficient cross-immunological relationship between the various strains of the C.M.V., and the novel strain provided by the present invention, that it has therefore the capability of protecting the population to a sufficiently great extent against the disease.

When large-scale production is required the attenuated C.M.V. strain is usually stored as a stock virus. Samples of this are then propagated, for instance on freshly prepared M.R.C.-5 cells in an appropriate medium, such as the the serum-free "Eagle's minimum essential medium" (M.E.M.) (Eagle H. Science 1959 130 432). When almost complete cytopathic effect becomes apparent, after 5-7 days of incubation, the cells are re-suspended and sonicated with the aid of an ultrasonic generator to facilitate the disintegration of the cells. The sonicated preparation may then be centrifuged at low speed to get rid of gross cell debris, and finally put through a sterilising filter.

It has been found convenient to store the virus suspension in serum free medium containing a stabiliser, such as 25% sorbitol. The formulation can then be frozen in ampules containing about 0.5 ml and stored in liquid nitrogen. Each batch should be tested for sterility and infectivity, and the ampules should contain about $10^7$ T.C.D.$_{50}$ units for each ml of liquid. For inoculation the contents may be diluted, for instance, in Hank's B.S.S. medium (Hanks, J. H. & Wallace, R. E. *Proc. Soc. exp. Biol.* 1949 71 196) to the required dose level, and the final titre confirmed, whenever necessary. Alternatively, the required single dosage or multiples thereof are presented in an ampoule, either in suspension or a frozen, dried or freeze-dried form.

In another aspect the invention provides a vaccine for developing immunity in humans against infections with C.M.V., which comprises an attenuated C.M.V. strain, as hereinbefore defined, in an effective dosage, or multiples thereof, in a pharmaceutically acceptable carrier. The effective dosage for vaccination may be from at least $3 \times 10^3$ to $3 \times 10^5$ T.C.D.$_{50}$ units. For subcutaneous administration the dose is usually from $5 \times 10^3$ to $3 \times 10^4$ T.C.D.$_{50}$ units, frequently around $10^4$ T.C.D.$_{50}$. For intradermal inoculation, the doses are higher, and are normally from $5 \times 10^4$ to $3 \times 10^5$ or more, preferably above $2 \times 10^5$ T.C.D.$_{50}$ units, to provide adequate protection.

The pharmaceutically acceptable carrier can be a liquid, such as an aqueous solution containing also nutrients and stabilizers, e.g. Hank's B,S.S. or other media. The same liquid carrier can also be present in a frozen state incorporating the virus particles. Furthermore, the carrier may, in some instances, include a sterile sealed container, such as an ampoule or vial, containing the virus particles, for instance, in a dried or freeze-dried state.

It can also be recognised that the invention provides, in a further aspect, a method for developing immunity in susceptible humans against infections with C.M.V., which comprises the parenteral administration of a vaccine, as hereinbefore defined, in the form of a suspension in a carrier. If necessary, a dried or frozen vaccine is resuspended and may then be injected under sterile conditions, for instance intradermally into the forearm, or subcutaneously into the delta region of the upper arm.

The effectiveness of the vaccine may be tested about one or two weeks later by determining the antibody titres and the absence of pathogenicity by observation of clinical symptoms and throat washings and urine tests.

Susceptible humans include many women, usually girls, who are already of child bearing age, but have not yet developed immunity in consequence of an earlier infection with C.M.V.

EXAMPLE 1

Preparation of the attenuated strain

The C.M.V. strain Ad 169 had 14 passages in M.A.F. cells (human embryonic fibroblasts, Microbiological Associates, Bethesda, U.S.A., cf. also Rowe, W. P. et al, *Proc. Soc. exp. Biol. Med.*, 1965, 92, 418) was obtained from Dr. Rowe as strain N.I.H. 76559. A further 10 passages were carried out in human foreskin fibroblasts, 4 passages in M.A.F. cells, 18 passages in diploid human embryonic lung fibroblasts (H.E.L.) and 8 passages in diploid human lung fibroblasts (M.R.C.-5 cells, cf. Jacobs, J. P. *et al, Nature,* 1970, 227, 168). The media used for the maintenance and propagation of these cells were Eagle's M.E.M. with 2-10% foetal calf serum, and transfers were carried out after 5 to 10 days of incubation. The resulting strain, in its 54th passage was then preserved in liquid nitrogen.

It was checked for freedom from extraneous organisms by culture on blood-agar and in nutrient broth (both aerobically and anaerobically), in mycoplasma medium, and by subculture on to various epithelial-cell tissue-cultures (on which C.M.V. does not grow) — i.e., human embryonic kidney, primary monkey kidney, and hela cells. It was also examined, after concentration by centrifugation at 40,000 rev/min for one hour, by electron-microscopy; bacteria or viruses other than C.M.V. were not seen.

Virus suspensions were titrated for infectivity in tube cultures of H.E.L. cells, using serial tenfold dilutions of the virus and five tubes per dilution. The cultures were refed twice weekly with Eagle's M.E.M. containing 2% foetal calf serum and observed for cytopathic effect over a period of three weeks. Infectivity titres were calculated by the Reed-Muench formula, and expressed as T.C.D.$_{50}$ (tissue culture infecting doses) per ml.

Complement-fixing (C.F.) antibodies were estimated by the standard microtitre technique, using cell-associated antigen prepared from the Ad 169 strain of virus, 2 units of complement, and overnight fixation of 4° C. Neutralising antibodies were determined by the plaque-reduction method (Plummer, G. *et al, Proc. Soc. exp. Med.* 1964, 145 and Haines H. G. *et al, Ibid,* 1971, 138, 864). In this method serial dilutions of heat-inactivated serum were incubated with equal volumes of virus suspension, diluted to contain approximately 300 plaque-forming units per 0.1 ml, in the presence of 2% fresh guinea pig serum, for one hour at 37° C. The reaction mixtures were then inoculated on to H.E.L.-cell monolayers and overlaid with 'Methocel'-gel medium. The antibody titre was calculated as the reciprocal of the highest dilution of serum which caused a 60% reduction in the number of plaques, when compared with the virus controls. C.M.V.-specific IgM antibodies were estimated by the indirect fluorescent-antibody technique, using Ad 169-infected H.E.L. cells, known positive and negative control human sera, and antihuman IgM antiserum conjugated with fluorescein isothiocyanate.

Tests were carried out with vaccines incorporating the attenuated C.M.V. strain, as hereinafter described in Examples 2 and 3, and confirmed that the strain fully retained its capability of inducing C.F. and neutralising antibodies in test subjects and had lost its pathogenicity to humans.

EXAMPLE 2

Preparation of a vaccine

Stock virus prepared according to Example 1 was used to prepare the necessary amount of virus for purposes of vaccine manufacture by infecting M.R.C.-5 cells, freshly prepared from their 16th or 17th passages. After 24 hours, the infected cell-cultures were washed three times with Hanks' balanced salt solution (B.S.S.) and then maintained on serum-free Eagle's minimum essential medium (M.E.M.). When the cultures showed 3 + to 4 + (almost complete) cytopathic effects, usually within 5 to 7 days, the cells were scraped down into the medium and the suspension was sonicated for 15 seconds at maximum amplitude in an MSE 150 watt ultrasonic disintegrator. Sorbitol solution was added to give a final concentration of 25% and the virus suspension was measured out as 0.5 ml volumes in hard-glass ampoules and stored in liquid nitrogen. Each batch was tested for sterility and was titrated in H.E.L. cells for infectivity; this was usually about $10^7$ T.C.D.$_{50}$ per ml. Aliquots (0.1 ml) of the batch were placed in sterile ampoules and sealed. When ever an ampoule was used for inoculation, the contents were diluted with Hanks' B.S.S. (20 ml) and 0.2 ml portions of this preparation were used for the inoculation. On each occasion the final infectivity of the inoculum given to volunteers was checked by titration on tissue-cultures.

The vaccines prepared in this manner were evaluated by vaccination tests in human volunteers, as described hereinafter in Example 3. It was found that unit dosages for vaccinating an individual gave satisfactory immunity when containing 2 or 3 × $10^5$ T.D.C.$_{50}$ units for intradermal inoculation, and $10^4$ or 2 × $10^4$ T.C.D.$_{50}$ units for subcutaneous treatment.

Ampoules, containing single doses, or multiples of 3, 5 and 10 of the required dosage, were prepared.

EXAMPLE 3

Vaccinations

Volunteers for test vaccinations were medical students and laboratory staff, both male and female. All volunteers were in good general health and had completely normal haematological and liver-function tests; the latter included tests for serum-bilirubin, alkaline phosphatase, thymol turbidity, serum-aspartate-aminotransferase (S.G.O.T.) and serum-alanine-aminotransferase (S.G.P.T.). Volunteers who had no detectable C.F. antibody in their serum, at 1 in 8 dilution, were regarded as susceptible to infection. Some volunteers who had antibody titres of 32 or greater were used as controls.

A. Vaccine inoculations were given intradermally into the left forearm by using 3 × $10^5$ T.C.D.$_{50}$ units in 0.2 ml. The same dose of virus, inactivated by heating at 56° C for twenty minutes was given into the right forearm. Two antibody negative, and one antibody positive, volunteers were given this dosage. Some skin lesions developed in the antibody negative volunteers at the site of the injection with live vaccine, but these rapidly deceased in size and disappeared after 3 weeks.

Blood was taken at intervals of one to two weeks for haematological and liver-function tests. Throat washings and urine from volunteers were collected directly into equal volumes of transport medium and inoculated without delay in 0.1 ml amounts into three H.E.L.-cell cultures each. These were re-fed twice weekly and observed for cytopathic effect for at least 4 weeks. On some occasions the specimens were first concentrated twenty-fold, by centrifugation at 40,000 rev/min for 1 hour, before being inoculated into tissue-cultures.

There was some enlargement of lymph-glands in both axillae, but those on the left side were larger and more tender. One of the volunteers also had slightly tender glands on the left side of the neck, causing some stiffness, and he had a "cold". This and the glandular enlargement appeared at the height of the local lesion, but lasted only a few days. On the tenth day numerous reactive lymphocytes developed in the blood of both volunteers without any other obvious haematological abnormality; by the twenty-first day the haematology was again normal. There was no disturbance of liver-function tests. Neither had detectable antibodies developed on the tenth day after inoculation, but at three weeks they had C.F. antibody titres of 32 and 64 and neutralising antibody titres of 160 and 160 respectively.

The single control volunteer with pre-existing antibody developed only a tiny red papule at the sites of the injection of both live and heated material after twenty-four hours, which increased slightly over the next day and then rapidly disappeared. His haematological tests remained normal and there was no change in his antibody titre. Virus could not be isolated from any of these 3 volunteers from throat washings or urine collected 1 week, 2 weeks, and 4 weeks after vaccination.

Four months later the 2 susceptible volunteers who had become seropositive were challenged with $10^5$ T.C.D.$_{50}$ of vaccine virus intradermally; the same dose of heated virus was given in the other arm. Both live and heated virus produced only a small reddish papule within 48 hours, which then quickly disappeared. The response seemed to be identical to that seen in the naturally immune volunteer. This challenge produced no significant change in antibody titre, and in the 2 successfully immunised volunteers both C.F. and neutralising antibody have persisted at unchanged levels for more than 2 years.

B. Four volunteers without pre-existing antibody were next given $10^4$ T.C.D.$_{50}$ and all 4 produced antibodies without important side-effects. Over a period, 26 susceptible volunteers were challenged with $10^4$ T.C.D.$_{50}$ of live vaccine virus subcutaneously (see table). In 14 of them there were no local symptoms at all. The other 12 noticed some itching over the site of inoculation, starting on the twelfth to fourteenth day, followed by a little aching. Palpation at that stage revealed a small area of induration and tenderness; only 1 volunteer had redness of the overlying skin. The symptoms mostly disappear within three to four days; in 3 cases they persisted for about a week. 1 of the 12 individuals with local symptoms also had slightly enlarged, tender glands in the left axilla and left side of the neck and this was associated with some reactive lymphocytes in the blood. The glands subsided within a week but reactive lymphocytes persisted for about 6 weeks. Another had some enlarged glands in the axilla which persisted for about three weeks but without associated reactive lymphocytes. Only one of those volunteers who had no local symptoms had mild axillary adenitis, which was noticed at 3 weeks and which had resolved within a further week. None of the volunteers demonstrated any disturbance of liver-function tests throughout the 8 weeks of observation.

25 of the 26 volunteers given $10^4$ T.C.D.$_{50}$ of live virus became seropositive. C.F. antibodies were dectable within two weeks in 11 volunteers and within three to eight weeks in the other 14 (see table). In all, peak titres were achieved within 6 to 8 weeks. Twenty-five volunteers have so far been followed up for a year and although 19 of them appear to have lost their C.F. antibodies there is no significant loss of neutralising antibodies. The single volunteer in whom antibodies did not develop had neither local nor general symptoms after vaccination.

Virus excretion was not demonstrated in any of the volunteers, although throat washings and urine specimens were examined weekly for six weeks. Twelve volunteers were studied more intensively, by daily collection of specimens, for evidence of excretion. Specimens were collected daily during the second week after vaccination from four of them, from another four during the third week, and from the remaining four during the fourth and fifth weeks. A final specimen was obtained from all twelve after 8 weeks. In no case was C.M.V. isolated.

A single volunteer with a pre-existing low level of C.F. antibody (C.F. titre 16) was also challenged with $10^4$ T.C.D.$_{50}$ of virus subcutaneously. He demonstrated no local reaction, but his antibody titre increased to 64 after 3 weeks.

A still higher dose of $10^5$ T.C.D.$_{50}$ was tested for four susceptible volunteers (see table). Three of them acquired antibodies within 3 to 4 weeks and two of these were the only volunteers, so far, in whom significant amounts of C.M.V.-specific IgM antibody developed; the titres were 10 and 40 respectively 3 weeks after inoculation and they persisted for at least a further three weeks. The symptoms in these three volunteers were no more severe than in those given $10^4$ T.C.D.$_{50}$. They had some local aching and tenderness at twelve to fourteen days and one also had some enlargement of the homolateral axillary lymph-glands. The symptoms had gone within another seven to ten days and there were no abnormalities in the haematological or liver-function tests. The one volunteer in whom antibody did not develop, even after three months, was the only one of the four to have no local reaction at all.

It was therefore concluded that the vaccine gave adequate protection in at least 96% of the subjects, with acceptable minimal side effects and no evidence of excretion in any form.

C.F. ANTIBODY RESPONSES IN SUSCEPTIBLE VOLUNTEERS GIVEN VARIOUS DOSES OF C.M.V. VACCINE SUBCUTANEOUSLY

| Vaccine dose (T.C.D.$_{50}$) | C.F. antibody titres at | | | |
|---|---|---|---|---|
| | — | 2 wk | 4 wk | 8 wk |
| $10^4$ | <8 | <8 | 32 | 32 |
| | <8 | <8 | 32 | 32 |
| | <8 | <8 | 32 | 64 |
| | <8 | <8 | 8 | 64 |
| | <8 | <8 | 32 | 32 |
| | <8 | — | 32 | 32 |
| | <8 | — | 64 | 32 |
| | <8 | <8 | 64 | 128 |
| | <8 | 16 | 32 | 32 |
| | <8 | 32 | 128 | 64 |
| | <8 | 32 | 128 | 128 |
| | <8 | <8 | 32 | 128 |
| | <8 | 32 | 32 | 32 |
| | <8 | 64 | 64 | 64 |
| | <8 | 32 | 128 | 128 |
| | <8 | 32 | 32 | 32 |
| | <8 | 8 | 32 | 32 |
| | <8 | <8 | 16 | 32 |
| | <8 | <8 | 32 | 128 |
| | <8 | 32 | 32 | 32 |
| | <8 | <8 | 128 | 128 |
| | <8 | <8 | 128 | 128 |
| | <8 | <8 | 32 | 32 |
| | <8 | <8 | <8 | <8 |
| | <8 | 16 | 32 | 64 |
| $10^5$ | <8 | <8 | 128 | 64 |
| | <8 | <8 | <8 | <8 |
| | <8 | <8 | 32 | 32 |
| | <8 | <8 | 32 | 128 |

We claim:

1. A method of preparing an attenuated strain of cytomegalovirus comprising serially passaging at least 40 times a cytomegalovirus isolate in susceptible human fibroblast cell cultures to obtain a virus strain which stimulates the production of complement fixing and neutralising antibodies in susceptible humans, when tested about 10 weeks after the subcutaneous administration of $10^4$ T.C.D.$_{50}$ units of the strain, without any significant side effects lasting longer than 1 to 2 weeks, or detectable excretions of the virus from the test subjects.

2. A method as claimed in claim 1 wherein the virus is passaged at least 8 times in each of the following types of cells, human embryonic fibroblasts, human foreskin fibroblasts and diploid human embryonic lung fibroblasts.

3. A vaccine for immunising susceptible humans against infections with cytomegalovirus, comprising an attenuated strain of cytomegalovirus prepared by the process of claim 1 in a pharmaceutically acceptable carrier in an effective dosage or multiples thereof for the vaccination of susceptible humans.

4. A vaccine as claimed in claim 3 in which the effective dosage for vaccination is from at least $3 \times 10^3$ to $3 \times 10^5$ T.C.D.$_{50}$ units.

5. A vaccine as claimed in claim 3 in which the carrier is an aqueous medium.

6. A vaccine as claimed in claim 5 in which the carrier is a saline or phosphate-buffered saline solution.

7. A vaccine as claimed in claim 5 in which the carrier also contains nutrients.

8. A vaccine as claimed in claim 3 in which the carrier contains a freeze-drying excipient.

9. A vaccine as claimed in claim 8 in which the freeze-drying excipient contains a stabiliser.

10. A vaccine as claimed in claim 9 in which the stabiliser is sorbitol or degraded gelatine.

11. A vaccine as claimed in claim 3 in which the carrier is a sealed sterile container suitable for long term storage.

12. A method for developing immunity in susceptible humans against infections with cytomegalovirus, comprising the parenteral administration of an effective dosage of the vaccine as claimed in claim 3, in the form of a suspension in a carrier.

13. A method as claimed in claim 12 in which the vaccine is administered by intradermal injection.

14. A method as claimed in claim 12 in which the vaccine is administered by subcutaneous injection.

15. The method of claim 1 in which the cytomegalovirus passaged is strain N.I.H. 76559.

16. A vaccine for immunising susceptible humans against infections with cytomegalovirus, comprising an attenuated strain of cytomegalovirus prepared by the process of claim 15 in a pharmaceutically acceptable carrier in an effective dosage or multiples thereof for the vaccination of susceptible humans.

* * * * *